US005744156A

United States Patent [19]
De Lacharriere et al.

[11] Patent Number: 5,744,156
[45] Date of Patent: Apr. 28, 1998

[54] USE OF A SUBSTANCE P ANTAGONIST FOR THE TREATMENT OF SKIN REDDENING OF NEUROGENIC ORIGIN

[75] Inventors: Olivier De Lacharriere, Paris; Lionel Breton, Versailles, both of France

[73] Assignee: Société L'Oréal S.A., Paris, France

[21] Appl. No.: 574,856

[22] Filed: Dec. 19, 1995

[30] Foreign Application Priority Data

Dec. 19, 1994 [FR] France .................................. 94 15252

[51] Int. Cl.⁶ .......................................... A61L 15/44
[52] U.S. Cl. ................................. 424/445; 424/443
[58] Field of Search ........................ 424/443, 445

[56] References Cited

U.S. PATENT DOCUMENTS 5,565,462  10/1996  Eitan et al. .............................. 514/462

FOREIGN PATENT DOCUMENTS 0577394  1/1994  European Pat. Off. .

OTHER PUBLICATIONS

British Journal of Pharmacology, vol. 106, No. 2, 1992, pp. 256–262.
European Journal of Pharmacology, vol. 85, 1982, pp. 171–176.
Science (Wash. D.C.), 214 (4524), 1981, 1029–1031.
Ann. Intern. Med., 1981, 95/4 (468–476), USA.
Agents Actions, 1983, 13/2–3 (105–116), Switzerland.
British Journal of Phamacology, vol. 109, No. 1, 1993, pp. 259–264.
British Journal of Pharmacology, Dec. 1993, 119 (4), pp. 1614–1620.
British Journal of Pharmacology, vol. 105, No. 3, 1992, pp. 527–530.

*Primary Examiner*—Carlos Azpuru
*Attorney, Agent, or Firm*—Burns, Doane, Swecker & Mathis, L.L.P.

[57] ABSTRACT

The invention relates to the use of a substance P antagonist for the preparation of a pharmaceutical composition, especially for topical application, for treating skin reddening of neurogenic origin, and especially rosacea and pudic erythema.

The substance P antagonist may be a peptide compound or a nitrogen-containing compound or a nitrogen-containing, sulphur-containing or oxygen-containing heterocyclic compound.

32 Claims, No Drawings 5,744,156

USE OF A SUBSTANCE P ANTAGONIST FOR THE TREATMENT OF SKIN REDDENING OF NEUROGENIC ORIGIN

FIELD OF THE INVENTION

The present invention relates to the use of a substance P antagonist for the preparation of a pharmaceutical composition for treating rosacea and/or pudic erythema.

More particularly, this composition allows the treatment, by topical or oral administration or by injection, of rosacea or of pudic erythema.

DESCRIPTION OF THE PRIOR ART

Rosacea is a cutaneous infection characterized by an erythema of the face which is predominant on the cheekbones, the forehead and the nose, a hyperseborrhoea of the face in the region of the forehead, the nose and the cheeks, and by an infectious component with acneform pustules.

Moreover, a neurogenic component is associated with these signs, that is to say hyperreactivity of the skin of the face and of the neck, characterized by the appearance of reddening and of subjective sensations of the itching or pruritus type, of sensations of burns or of inflammation, of sensations of pricking, of formication, of discomfort, of stabbing pain and the like.

These signs of hyperreactivity may be triggered by various factors such as the intake of food, hot or alcoholic drinks, by rapid variations in temperature, by heat and especially exposure to ultraviolet or infrared light, by a low relative humidity, by exposing the skin to violent winds or to air currents (fan, air conditioner), by the application of surfactants, of irritant dermatological topical agents (retinoids, benzoyl peroxide, alpha-hydroxy acids and the like) or the use of certain cosmetics even when these are not known to be particularly irritant.

Up until now, the mechanism for triggering these signs was poorly known and rosacea was treated with active agents such as antiseborrhoeic agents and agents for combating infection, for example benzoyl peroxide, retinoic acid, metronidazole or the cyclines which acted on infection and hyperseborrhoea, but did not make it possible to treat the neurogenic component of this condition, and especially hyperreactivity of the skin and reddening.

Likewise, there was up until now no treatment for the reddening which appears in pudic erythema. The latter occurs during an emotional reaction and is characterized by reddening of the face and of the neck and shoulders, which may possibly be accompanied by pruritus (itching). This condition is very uncomfortable for the individuals suffering from it, and up until now it could only be treated with beta-blockers, potent drugs which are used to treat hypertension and which have numerous contraindications.

The need therefore remains for a treatment of cutaneous reddening, an essential component of this state of hyperreactivity of skin affected by rosacea or pudic erythema.

SUMMARY OF THE INVENTION AND PREFERRED EMBODIMENTS

The subject of the present invention is precisely the use of one or more substance P antagonists for treating these conditions.

Substance P is a polypeptide chemical element produced and released by a nerve ending. It is part of the family of tachykinins which are obtained from the free nerve endings of the epidermis and of the dermis. Substance P is involved especially in the transmission of pain and in diseases of the central nervous system such as anxiety, schizophrenia, in respiratory and inflammatory diseases, in gastrointestinal diseases, in rheumatic diseases and in certain dermatological diseases such as eczema, psoriasis, urticaria and contact dermatitis.

It is known to use substance P antagonists for treating the diseases indicated above. To this end, reference may be made to the documents U.S. Pat. No. 4,472,305, U.S. Pat. No. 4,839,465, EP-A-101929, EP-A-333174, : EP-A-336230, EP-A-394989, EP-A-443132, EP-A-498069, EP-A-515681, EP-A-517589, WO-A-92/22569, GB-A-2216529, EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116, EP-A-522808, WO-A-93/01165, WO-A-93/10073 and WO-A-94/08997.

However, until now no one had considered using them to treat cutaneous reddening of neurogenic origin.

Accordingly, the subject of the present invention is the use of at least one substance P antagonist for the preparation of a pharmaceutical or dermatological composition for treating cutaneous reddening of neurogenic origin, especially due to the release of tachykinins.

The subject of the present invention is more particularly the use of a substance P antagonist for the preparation of a pharmaceutical or dermatological composition for treating rosacea and/or pudic erythema.

The application of compositions containing one or more substance P antagonists makes it possible to obtain a sharp decrease or even a complete disappearance of the reddening which manifests itself both in rosacea and in pudic erythema.

The substance P antagonist therefore acts on the neurogenic component of these conditions, for which there was no treatment up until now, and thus reinforces the efficacy of the active agents used up until now for the treatment of their infectious component, especially in the case of rosacea.

The composition of the invention contains a pharmaceutically or dermatologically acceptable medium, that is to say a medium which is compatible with the skin, the nails, the mucous membranes, the tissues and the hair. The composition containing the substance P antagonist may be applied topically to the face, the neck, the hair, the mucous membranes and the nails, large skin-folds or any other cutaneous region of the body. It may also be administered orally or injected.

For a substance to be recognized as a substance P antagonist, it should meet the following characteristic:
  it should have a pharmacological activity which antagonizes substance P, that is to say it should induce a coherent pharmacological response in at least one of the following two tests:
  the antagonistic substance should reduce extravasation of the plasma through the vascular wall induced by capsaicin or by an antidromic nervous stimulation, or alternatively
  the antagonistic substance should cause inhibition of the contraction of the smooth muscles induced by the administration of substance P.

The substance P antagonist may, in addition, have a selective affinity for the NK1 receptors for tachykinins.

The substance P antagonist of the invention may be functional or a receptor, that is to say may inhibit the synthesis and/or the release of substance P, or may prevent its binding and/or modulate its action.

The substance P antagonist of the invention may be chosen from peptides or nonpeptide derivatives, and more specifically those containing a nitrogen-, sulphur- or oxygen-containing heterocycle, or the nitrogen-containing compounds containing a nitrogen atom linked directly or indirectly to a benzene ring.

Sendide and spantide II may be used in the invention, for example, as substance P-antagonizing peptide.

Sendide corresponds to the formula:

in which:

Tyr represents tyrosine,

D-Phe represents D-phenylalanine,

Phe represents phenylalanine,

D-His represents D-histidine,

Leu represents leucine,

Met represents methionine.

Spantide II corresponds to the formula:

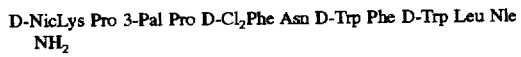

in which:

D-NicLys represents D-lysine nicotinate,

Pro represents proline,

3-Pal represents 3-pyridyl-alanine,

D-Cl$_2$Phe represents D-dichlorophenylalanine,

Asn represents asparagine,

D-Trp represents D-tryptophan,

Phe represents phenylalanine,

Leu represents leucine,

Nle represents norleucine.

The peptides described in the documents U.S. Pat No. 4,472,305, U.S. Pat. No. 4,839,465, EP-A-101929, EP-A-333174, EP-A-336230, EP-A-394989, EP-A-443132, EP-A-498069, EP-A-515681, EP-A-517589, WO-A-92/22569 and GB-A-2216529 may also be used in the invention as substance P-antagonizing peptide.

Nonpeptide substance P antagonists which can be used in the invention are especially heterocyclic compounds, especially nitrogen-, sulphur- or oxygen-containing heterocyclic compounds, or compounds comprising a nitrogen atom linked directly or indirectly to a benzene ring.

As heterocyclic compound, there may be used in the invention those containing a nitrogen-containing heterocycle which are described in the following documents: EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116 and WO-A-94/08997. In particular, the compound comprising at least one nitrogen-containing heterocycle is a 2-tricyclyl-2-aminoethane derivative, a spirolactam derivative, a quinuclidine derivative, an azacyclic derivative, an aminopyrrolidine derivative, a piperidine derivative, an aminoazaheterocycle, an isoindole derivative.

As other heterocyclic compounds, there may be mentioned the oxygen- or sulphur-containing heterocyclic compounds such as furan derivatives, benzofuran derivatives, thiophene derivatives, benzothiophene derivatives, optionally containing nitrogen-containing substituents, such as the heterocyclic compounds described in the documents U.S. Pat. Nos. 4,931,459, 4,910,317 and EP-A-299457, and more especially the alkoxy and/or aryloxytetrazolyl-benzofuran-carboxamides or the alkoxy- and/or aryloxy-tetrazolylbenzothiophene-carboxamides.

As compounds containing a nitrogen atom linked directly or indirectly to a benzene ring, there may be mentioned those described in the following documents: EP-A-522808, WO-A-93/01165 and WO-A-93/10073. There may be mentioned especially the ethylenediamine derivatives, such as N,N'-bis-di(3,5-dimethylbenzyl)ethylenediamine, N,N'-bis-di(3,5-dimethoxybenzyl)ethylenediamine; these compounds are described as synthesis intermediates in the document WO-A-93/11338 filed in the name of the applicant.

The substance P antagonists may be synthesized or may be extracts of natural products (plant or animal products).

In the compositions according to the invention, the substance P antagonist is preferably used in a quantity ranging from 0.000001 to 5% by weight relative to the total weight of the composition, and in particular in a quantity ranging from 0.0001 to 0.1% by weight relative to the total weight of the composition.

The compositions according to the invention may be presented in all the galenic forms normally used depending on the route of administration (injection, oral, topical).

For a topical application, the composition may be provided especially in the form of aqueous, aqueous-alcoholic or oily solutions, or of dispersions of the lotion or serum type, of emulsions of liquid or semiliguid consistency of the milk type, which are obtained by dispersion of a fatty phase in an aqueous phase (O/W) or conversely (W/O), or of suspensions or emulsions of soft, semisolid or solid consistency of the cream or gel type, of microemulsions, or alternatively of microcapsules, of microparticles, or of vesicular dispersions of the ionic and/or nonionic type. They may also be packaged in the form of an aerosol composition also containing a pressurized propelling agent. These compositions are prepared according to the customary methods.

They may also be used for the scalp in the form of aqueous, alcoholic or aqueous-alcoholic solutions, or in the form of creams, gels, emulsions, foam, or alternatively of an aerosol composition.

The injectable compositions may be presented in the form of an aqueous or oily lotion or in the form of a serum.

The compositions used orally may be presented in the form of capsules, gelatin capsules, syrups or tablets.

The quantities of the different constituents of the compositions according to the invention are those conventionally used in the fields considered.

These compositions constitute especially protective, treatment or care creams for the face, hands, feet, large anatomical skin-folds or for the body, protective or care body milks, lotions, gels or foams for the care of the skin and of the mucous membranes, such as cleansing or disinfectant lotions, compositions for the bath, compositions containing a bactericidal agent.

The compositions may also consist of solid preparations constituting soaps or cleansing bars.

When the composition of the invention is an emulsion, the proportion of fatty phase may range from 5% to 80% by weight, and preferably from 5% to 50% by weight relative to the total weight of the composition. The oils, emulsifiers and coemulsifiers used in the composition in the form of an emulsion are chosen from those conventionally used in the dermatological field. The emulsifier and coemulsifier are present, in the composition, in a proportion ranging from 0.3% to 30% by weight, preferably from 0.5 to 20% by weight relative to the total weight of the composition. The emulsion may, in addition, contain lipid vesicles.

When the composition is an oily solution or gel, the quantity of oil may range up to more than 90% by weight of the total weight of the composition.

In a known manner, the composition of the invention may also contain the usual adjuvants in the fields considered, such as hydrophilic or lipophilic gelling agents, hydrophilic or lipophilic active agents, preservatives, antioxidants, solvents, perfumes, fillers, sunscreens, odour absorbers and colouring matter. The quantities of these different adjuvants are those conventionally used in the fields considered, and are for example from 0.01% to 10% of the total weight of the composition. These adjuvants, depending on their nature, may be introduced into the fatty phase, into the aqueous phase and/or into the lipid spherules.

As oils which can be used in the invention, there may be mentioned mineral oils (liquid paraffin), vegetable oils (liquid fraction of shea butter, sunflower oil), animal oils (perhydrosqualene), synthetic oils (Purcellin oil), silicone oils (cyclomethicone) and fluorinated oils (perfluoropolyethers). Fatty alcohols and fatty acids (stearic acid) may be added to these oils.

As emulsifiers which can be used in the invention, there may be mentioned for example glycerol stearate, polysorbate 60 and the PEG-6/PEG-32/glycol stearate mixture sold under the name Tefose® 63 by the company Gattefosse.

As solvents which can be used in the invention, the lower alcohols, especially ethanol and isopropanol may be mentioned.

As hydrophilic gelling agents, there may be mentioned the carboxyvinyl polymers (carbomer), the acrylic copolymers such as the copolymers of acrylate/alkyl acrylates, polyacrylamides, polysaccharides such as hydroxypropyl cellulose, clays and natural gums, and, as lipophilic gelling agents, there may be mentioned modified clays such as bentones, the metal salts of fatty acids such as aluminium stearates, hydrophobic silica, polyethylenes and ethyl cellulose.

As hydrophilic active agents, proteins or protein hydrolysates, amino acids, polyols, urea, allantoin, sugars and sugar derivatives, vitamins, plant extracts, especially from Aloe vera, and hydroxy acids can be used.

As lipophilic active agents, tocopherol (vitamin E) and its derivatives, retinol (vitamin A) and its derivatives, essential fatty acids, ceramides and essential oils may be used.

The substance P antagonists may also be combined with active agents, especially decongestants, antibacterials, antiseptics and antimicrobials.

Among these active agents, there may be mentioned by way of example:

antiseptics such as salicylic acid and its derivatives (n-octanoyl-5-salicylic acid), or crotamiton;

antibacterials such as clindamycin phosphate, erythromycin or antibiotics of the class of tetracyclines;

antiparasitic agents, in particular metronidazole or pyrethrinoids;

antifungal agents, in particular compounds belonging to the family of imidazols such as econazol, keoconazol or miconazol or their salts, polyene compounds, such as amphotericin B, compounds of the family of allyl amines, such as terbinafine, or alternatively octopirox;

steroidal anti-inflammatory agents such as hydrocortisone, betamethasone valerate or clobetasol propionate, or non-steroidal anti-inflammatory agents such as ibuprofen and its salts, diclofenac and its salts, acetylsalicylic acid, acetaminophen or glycyrrhetinic acid;

anaesthetic agents such as lidocaine hydrochloride and its derivatives;

antipruritic agents such as thenaldine, trimeprazine or cyproheptadine;

anti-free radical agents such as alpha-tocopherol or its esters, superoxide dismutases, certain metal chelators or ascorbic acid and its esters;

keratolytic agents such as 13-cis- or all-trans-retinoic acid, benzoyl peroxide or hydroxy acids.

The following examples illustrate the invention. In these examples, the proportions indicated are percentages by weight.

EXAMPLE 1

Face Cream (oil-in-water emulsion)

| | | |
|---|---|---|
| Spantide II | | 0.3% |
| Glycerol stearate | | 2% |
| Polysorbate 60 (Tween 60 sold by the company ICI) | | 1% |
| Stearic acid | | 1.4% |
| Triethanolamine | | 0.7% |
| Carbomer | | 0.4% |
| Cyclomethicone | | 8% |
| Sunflower oil | | 12% |
| Antioxidant | | 0.05% |
| Preservative | | 0.3% |
| Water | qs | 100% |

EXAMPLE 2

Emulsified Gel (oil-in-water emulsion)

| | | |
|---|---|---|
| Cyclomethicone | | 3.00 |
| Purcellin oil (sold by the company Dragocco) | | |
| PEG-6/PEG-32/glycol stearate (Tefose ® 63 from Gattefosse) | | 0.30 |
| N,N'-bis-di(3,5-dimethoxybenzyl)ethylenediamine | | 0.5 |
| Preservative | | 0.30 |
| Carbomer | | 0.60 |
| Crotamiton | | 5.00 |
| Glycyrrhetinic acid | | 2.00 |
| Ethyl alcohol | | 5.00 |
| Triethanolamine | | 0.20 |
| Water | qs | 100% |

EXAMPLE 3

Gel

| | |
|---|---|
| All-trans-retinoic acid | 0.05% |
| N,N'-bis-di(3,5-dimethylbenzyl)-ethylenediamine | 5% |
| Hydroxypropyl cellulose (Klucel H sold by the company Hercules) | 1% |
| Antioxidant | 0.05% |

-continued

| | | |
|---|---|---|
| Isopropanol | | 40% |
| Preservative | | 0.3% |
| Water | qs | 100% |

EXAMPLE 4

Cream (oil-in-water emulsion)

| | | |
|---|---|---|
| Spantide II | | 0.25 |
| Glycerol stearate | | 2.00 |
| Polysorbate 60 (Tween 60 sold by the company ICI) | | 1.00 |
| Stearic acid | | 1.40 |
| Metronidazole | | 0.50 |
| Triethanolamine | | 0.70 |
| Carbomer | | 0.40 |
| Cyclomethicone | | 8.00 |
| Sunflower oil | | 10.00 |
| Antioxidant | | 0.05 |
| Preservative | | 0.30 |
| Water | qs | 100% |

We claim:

1. A method for treating cutaneous reddening of neurogenic origin comprising topically applying a pharmaceutical or dermatological composition containing an effective amount of at least one substance P antagonist.

2. The method of claim 1, wherein the substance P antagonist is a peptide.

3. The method of claim 1, wherein the substance P antagonist is a heterocyclic compound.

4. The method of claim 1, wherein the substance P antagonist is a benzene ring containing nitrogen compound.

5. The method of claim 1, wherein the substance P antagonist is sendide or spantide II.

6. The method according to claim 1, wherein the substance P antagonist is selected from the group consisting of 2-tricyclyl-2-aminoethane compounds, spirolactam compounds, quinuclidine compounds, azacyclic compounds, aminopyrrolidine compounds, piperidine compounds, aminoazaheterocyclic compounds, or isoindole compounds.

7. The method of claim 1, wherein the substance P antagonist is an oxygen or sulfur containing heterocyclic compound selected from the group consisting of furan compounds, benzofuran compounds, thiophene compounds, or benzothiophene compounds.

8. The method of claim 7, wherein the substance P antagonist is a tetrazolylbenzofuran-carboxamide or tetrazolylbenzo-thiophene-carboxamide.

9. The method of claim 1, wherein the substance P antagonist is an ethylenediamine compound.

10. The method of claim 1, wherein the substance P antagonist is contained in an amount ranging from 0.000001 to 5% by weight relative to the total weight of the composition.

11. The method of claim 10, wherein the substance P antagonist is contained in an amount ranging from 0.0001 to 0.1% by weight relative to the total weight of the composition.

12. The method according to claim 1, wherein the topically applied composition further contains another agent selected from the group consisting of proteins, protein hydrolysates, amino acids, polyols, urea, sugars, vitamins, starches, plant extracts, hydroxy acids, ceramides and essential oils.

13. The method according to claim 1, wherein the topically applied composition further comprises another agent selected from the group consisting of antiseptic, antibacterial, antiparasitic, antifungal, anti-inflammatory, antipruritic, anaesthetic, antiviral, keratolytic and anti-free radical agents.

14. The method according to claim 1, wherein the composition is selected from the group consisting of aqueous, oily and aqueous-alcoholic solutions, water-in-oil emulsions, oil-in-water emulsions, microemulsions, aqueous gels, anhydrous gels, serums, vesicle containing dispersions, microcapsule containing dispersions and microparticle containing dispersions.

15. The method of claim 1, wherein the substance P antagonist exhibits a pharmacological response in at least one of the following tests:

(i) reduces the extravasation of the plasma through the vascular wall induced by capsaicin or by an antidromic nervous stimulation; or (ii) causes inhibition of smooth muscle contraction induced by substance P administration.

16. The method of claim 15, wherein the substance P antagonist further possesses selective affinity for the NK1 receptors of tachykinins.

17. A method of treating at least one of rosacea and pudic erythema comprising topically applying a pharmaceutical or dermatological composition containing an effective amount of at least one substance P antagonist.

18. The method of claim 17, wherein the substance P antagonist is a peptide.

19. The method of claim 17, wherein the substance P antagonist is a heterocyclic compound.

20. The method of claim 17, wherein the substance P antagonist is a benzene ring containing nitrogen compound.

21. The method of claim 17, wherein the substance P antagonist is sendide or spantide II.

22. The method according to claim 17, wherein the substance P antagonist is selected from the group consisting of 2-tricyclyl-2-aminoethane compounds, spirolactam compounds, quinuclidine compounds, azacyclic compounds, aminopyrrolidine compounds, piperidine compounds, aminoazaheterocyclic compounds, or isoindole compounds.

23. The method of claim 17, wherein the substance P antagonist is an oxygen or sulfur containing heterocyclic compound selected from the group consisting of furan compounds, benzofuran compounds, thiophene compounds, or benzothiophene compounds.

24. The method of claim 23, wherein the substance P antagonist is a tetrazolylbenzofuran-carboxamide or tetrazolylbenzo-thiophene-carboxamide.

25. The method of claim 17, wherein the substance P antagonist is an ethylenediamine compound.

26. The method of claim 17, wherein the substance P antagonist is contained in an amount ranging from 0.000001 to 5% by weight relative to the total weight of the composition.

27. The method of claim 26, wherein the substance P antagonist is contained in an amount ranging from 0.0001 to 0.1% by weight relative to the total weight of the composition.

28. The method according to claim 17, wherein the topically applied composition further contains another agent selected from the group consisting of proteins, protein hydrolysates, amino acids, polyols, urea, sugars, vitamins, starches, plant extracts, hydroxy acids, ceramides and essential oils.

29. The method according to claim 17, wherein the topically applied composition further comprises another agent selected from the group consisting of antiseptic, antibacterial, antiparasitic, antifungal, anti-inflammatory, antipruritic, anaesthetics antiviral, keratolytic and anti-free radical agents.

30. The method according to claim 17, wherein the composition is selected from the group consisting of aqueous, oily and aqueous-alcoholic solutions, water-in-oil emulsions, oil-in-water emulsions, microemulsions, aqueous gels, anhydrous gels, serums, vesicle containing dispersions, microcapsule containing dispersions and microparticle containing dispersions.

31. The method of claim 17, wherein the substance P antagonist exhibits a pharmacological response in at least one of the following tests:
   (i) reduces the extravasation of the plasma through the vascular wall induced by capsaicin or by an antidromic nervous stimulation; or
   (ii) causes inhibition of smooth muscle contraction induced by substance P administration.

32. The method of claim 15, wherein the substance P antagonist further possesses selective affinity for the NK1 receptors of tachykinins.

* * * * *